US00PP16681P2

(12) United States Plant Patent
Utecht

(10) Patent No.: US PP16,681 P2
(45) Date of Patent: Jun. 20, 2006

(54) *GERANIUM* PLANT NAMED 'FISLINA'

(50) Latin Name: *Pelargonium peltatum*
Varietal Denomination: Fislina

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 90 days.

(21) Appl. No.: 10/998,560

(22) Filed: Nov. 30, 2004

(51) Int. Cl.
*A01H 5/00* (2006.01)

(52) U.S. Cl. ..... Plt./332
(58) Field of Classification Search ..... Plt./332
See application file for complete search history.

(56) References Cited

PUBLICATIONS

German PBR Application No. PEL 1893 filed Jun. 4, 2003 and withdrawn Oct. 5, 2004 (Copy of German Gazettes dated 1) Jul. 15, 2003—Listing Assigned Application for Protection Number (2 pgs), 2) May 15, 2004—Publishing Proposed Variety Denomination (2 pgs), and 3) Nov. 15, 2004—Listing Withdrawal of Application for Protection (2 pgs)).

Canadian PBR Application No. 03–3897 filed Nov. 21, 2003 (Copy of Canadian Plant Varieties Journal dated Jan., 2004 Listing Assigned Application Number (2 pgs).

Community Plant Variety Office (CPVO) No. 2004/1248 filed Jul. 5, 2004 (Copy of Official Gazette of the CPVO dated Oct. 15, 2004 Listing Assigned Application Number and Variety Denomination (3 pgs).

Fischer 2005 catalogue offering 'Fislina' (with shipment of plant material available starting Dec. 2004) (3 pgs).

*Primary Examiner*—Kent Bell
(74) *Attorney, Agent, or Firm*—Foley & Lardner LLP

(57) ABSTRACT

A new and distinct cultivar of *geranium* plant named 'Fislina', particularly characterized by the combined features of moderately large, salmon-pink, double flowers; medium-sized, semi-spherical inflorescences with initially short peduncles; green foliage, round leaves with narrow, ring-shaped zonation; initially round and bushy, and later, over medium sized and trailing plant habit; and early spring flowering response.

1 Drawing Sheet

Genus and species of the plant claimed: *Pelargonium peltatum* L'Héritier (hybrid).
Variety Denomination: 'Fislina'.

BACKGROUND OF THE INVENTION

The present invention comprises a new and distinct cultivar of *geranium*, botanically known as *Pelargonium peltatum*, and hereinafter referred to by the cultivar name 'Fislina'.

'Fislina' is a product of a planned breeding program which had the objective of creating new ivy *geranium* cultivars with semi-double to double flower type, zoned foliage, and about medium sized, well-branched growth habit, in various flower colors.

'Fislina' originated from a hybridization made by the inventor, Angelika Utecht, in a controlled breeding program in Hillscheid, Germany, in 1999. The female parent of 'Fislina' was the patented variety 'Fislunova' (U.S. Plant Pat. No. 12,329), and is described as having white, double flowers, medium green foliage with weak zonation, and medium tall plant habit. The male parent of 'Fislina' was the unpatented hybrid plant No. 95-338-5, which was characterized by red, single-type flowers, foliage with relatively strong zonation, and about medium (or over) growth habit.

'Fislina' was selected as one flowering plant within the progeny of the stated cross by Angelika Utecht in 2000 in a controlled environment on Fuerteventura, Canary Islands, Spain.

The first act of asexual reproduction of 'Fislina' was accomplished when vegetative cuttings were taken from the initial selection in the fall of 2000, in a controlled environment in Fuerteventura, Spain, by, or under the supervision of Angelika Utecht.

Horticultural examination of plants grown from cuttings of the plant initiated in May of 2000 in Hillscheid, Germany, and continuing thereafter, has demonstrated that the combination of characteristics as herein disclosed for 'Fislina' are firmly fixed and are retained through successive generations of asexual reproduction.

BRIEF SUMMARY OF THE INVENTION

'Fislina' has not been observed under all possible environmental conditions. The phenotype may vary significantly with variations in environment such as temperature, light intensity and day length. The following observations, measurements, and comparisons describe plants grown in Hillscheid, Germany, under greenhouse conditions which approximate those generally used in commercial practice.

The following traits have been repeatedly observed and are determined to be basic characteristics of 'Fislina' in combination distinguish this *geranium* as a new and distinct cultivar:

1. moderately large, double, salmon-pink colored flowers;
2. medium sized, semi-spherical inflorescences with initially short peduncles;
3. medium green foliage with distinct zonation;

4. characteristically shaped, round leaves;
5. over medium sized plant habit, only moderately tight; and
6. early spring flowering response.

Of the many commercial cultivars known to the present inventor, the most similar is the variety 'Fismoli' (U.S. Plant Pat. No. 9,382).

In comparison to 'Fismoli', 'Fislina' has a salmon-pink flower color of a less bluish, somewhat more orange-pink hue, and somewhat earlier beginning of flowering. Furthermore, inflorescences of 'Finlina' are borne on initially short, later medium peduncles, while 'Fismoli' develops long peduncles. Additionally, 'Fislina' has round leaves with only very weak lobes, while the leaves of 'Fismoli' are typically ivy-shaped.

BRIEF DESCRIPTION OF THE DRAWING

The accompanying photographic drawing shows typical flower and foliage characteristics of 'Fislina' with colors being as true as possible with an illustration of this type. The photographic drawing shows a side perspective view of a flowering potted plant of 'Fislina' with leaves, buds and inflorescences.

DETAILED BOTANICAL DESCRIPTION

The measurements were taken in Hillscheid, Germany, in mid May 2003, 15 weeks after planting of rooted cuttings. The plants were grown in 14 cm pots; they had been pinched once.

In the following description color references are made to The Royal Horticultural Society Colour Chart. The color values were determined indoors from plants growing in a green-house in May 2003, in Hillscheid, Germany.

Parentage:
- *Male parent.*—Unpatented, hybrid plant No. 95-338-5.
- *Female parent.*—'Fislunova' (U.S. Plant Pat. No. 12,329).

Classification: *Pelargonium peltatum* L'Héritier (hybrid).
Propagation: Vegetative cuttings.
Inflorescence: Umbel:
- *Shape.*—Semi-spherical.
- *Average diameter.*—81 mm.
- *Average depth.*—45 mm.

Peduncle:
- *Peduncle length.*—102 mm.
- *Peduncle diameter.*—3 mm.
- *Peduncle color.*—Light green, RHS 143 C.

Pedicel:
- *Pedicel length.*—21 mm in length, occasionally with a spur near the base of the flower.
- *Pedicel diameter.*—2 mm.
- *Pedicel color.*—Light green, RHS 143 C, to occasionally greyed-red, RHS 179 B.
- *Number of flowers per umbel.*—About 6–12.

Corolla:
- *Average length.*—55 mm.
- *Average width.*—50 mm.
- *Depth.*—20 mm.
- *Form.*—Double-type.
- *Shape.*—Oval outline.

Petaloids:
- *Number of petaloids.*—3–5.
- *Length.*—Variable, ranges from 10 to 15 mm.
- *Width.*—Variable, ranges from 2 to 8 mm.
- *Overall shape.*—Filiform (threadlike) to obovate, generally much narrower and somewhat shorter than the petals.
- *Apex shape.*—Acute to rounded.
- *Base shape.*—Acute or attenuate.
- *Margin.*—Mostly entire, occasionally with single notches.
- *Color of upper petaloids.*—Red, RHS 52 A.
- *Color of lower petaloids.*—Red, RHS 52 A.

Petals:
- *Number of petals.*—About 15–20.
- *Shape of petals.*—Obovate, base acute or attenuate, upper end is rounded, margin is entire or slightly crenate.
- *Size of petals.*—Upper petals: 30–32 mm long, 20–24 mm wide. Lower petals: 25–28 mm long, 18–22 mm wide.
- *Color (general tonality from a distance of three meters).*—Salmon-pink.
- *Color of upper petals.*—Between red, RHS 52A, and red, RHS 52 B, color may later turn towards red, RHS 55 A.
- *Markings of upper petals.*—Distinct, if not covered by inner petals: 2 dark red-purple veins, RHS 61 A, and a small dark red spot, RHS 46 A.
- *Color of lower petals.*—Red, near RHS 55 A.
- *Markings of lower petals.*—None.
- *Color of lower surface of petals.*—Red, approximately RHS 52 C, lighter near the margins, approximately from red, RHS 52 D, to red-purple, 58 D; at the base of upper petals dull violet veins are visible.

Sepals:
- *Color of sepals.*—Outer (lower) surface: largest sepal greyed-red, RHS 181 B; other sepals yellow-green, RHS 144 A; inner (upper surface) yellow-green, RHS 144 B.
- *Number of sepals.*—5.
- *Shape of sepals.*—Linear to lanceolate, acute tip, fused base, surface with weak pubescence, margin entire.
- *Size of sepals.*—13 mm long, 6–7 mm wide for the largest upper sepal, 3–4 mm in width for the other sepals.

Bud: (just prior to petals unfolding):
- *Shape.*—Elliptical, relatively short and wide.
- *Color of sepals.*—Light green, RHS 143 C, with slight pubescence.
- *Color of petals.*—Red, RHS 43 B.
- *Length.*—16 mm.
- *Width.*—9 mm.

Reproductive organs:
- *Androecium.*—5–7 fertile anthers, plenty pollen, range, RHS 28 A, lower side of anthers grayish, filaments white, RHS 155 D, to light-pink, RHS 52 D.
- *Gynoecium.*—One pistil, red-purple style and stigma, RHS 61 A, 5–6-lobed.
- *Fertility/seed set.*—Seed set was not observed.
- *Spring flowering response period.*—In Hillscheid, Germany, in 2003 plants had on average 0.9 flowers opened 12 weeks after planting of rooted cuttings (pinched plants).
- *Outdoor flower production.*—Continuously and rich flowering, the flower count in 2003 in Hillscheid, Germany, indicated about 20–30 inflorescence per plant in late summer.
- *Durability.*—Fair stability of flower, some fading may occur, fair rain resistance.

*Lastingness of the individual flower.*—About 8 days at 18° C.

*Fragrance.*—None.

Plant: Foliage:

*Overall shape.*—Nearly round to very weakly ivy-shaped.

*Base shape.*—Cordate base, with the gap between the lowest lobes just closed.

*Apex shape.*—Apex rounded with very weak lobes (for an ivy *geranium*).

*Margin.*—Entire.

*Texture.*—Upper surface smooth, slightly glossy.

*Size of leaf.*—83 mm wide, about 50 mm long.

*Color of upper surface.*—Medium green, closest to RHS 137 C.

*Zonation.*—A narrow ring, color: greyed-red, closest to RHS 166 A.

*Color of lower surface.*—Green, RHS 143 C.

*Petiole.*—85 mm long, 2–3 mm diameter, light green in color, RHS 143 B.

General appearance and form:

*Stem color.*—Light green, RHS 143 B.

*Internode length.*—25–35 mm.

*Branching pattern.*—5.8 branches on average.

*Size of plants.*—Height: 15.0 cm (15 week-old plants, as described). Diameter: 23 cm (15 week-old plants, as described). Length: 18.8 cm (15 week old plants, as described), and 75 cm (30 week-old plants, around September 1), measured from the top of the soil (base of the main stem) to the tips of the branches, without inflorescences.

I claim:

1. A new and distinct cultivar of *geranium* plant named 'Fislina', as described and illustrated herein.

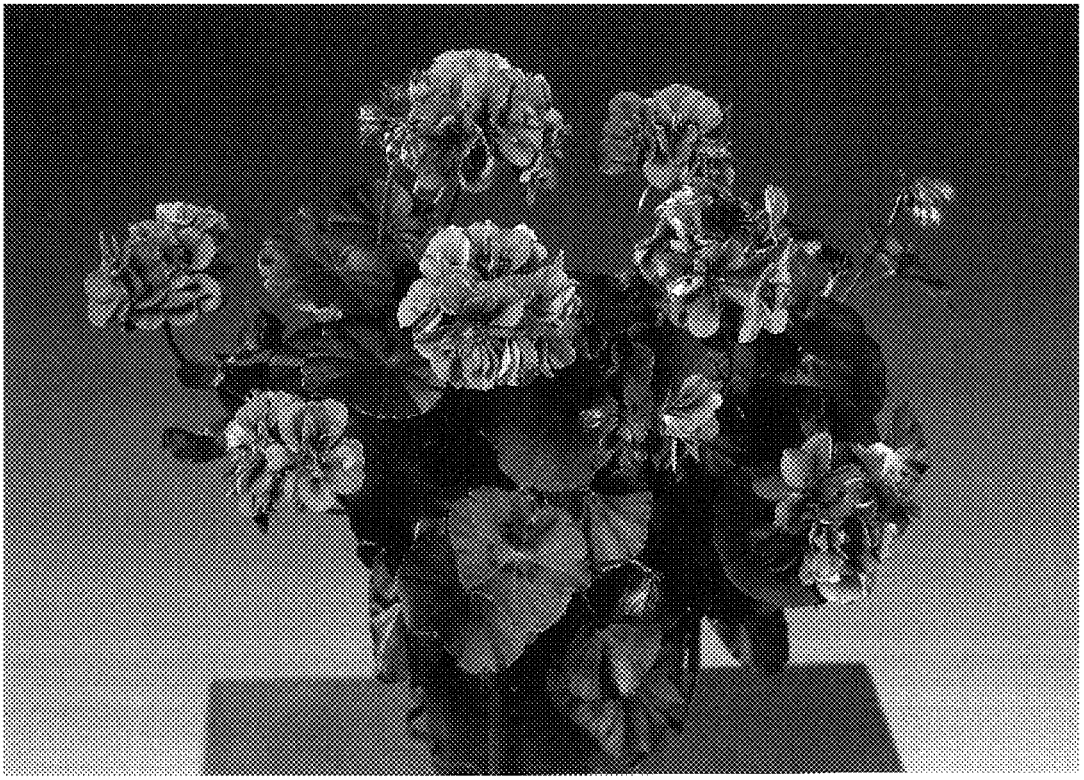

* * * * *